United States Patent [19]

Schön et al.

[11] Patent Number: 5,149,856
[45] Date of Patent: Sep. 22, 1992

[54] PROCESS FOR THE PREPARATION OF CARBONIC ACID DIESTERS CONTAINING AT LEAST ONE AROMATIC ESTER GROUP

[75] Inventors: Norbert Schön; Hans-Josef Buysch; Wolfgang Ebert, all of Krefeld, Fed. Rep. of Germany

[73] Assignee: Bayer Aktiengesellschaft, Leverkusen, Fed. Rep. of Germany

[21] Appl. No.: 657,930

[22] Filed: Feb. 20, 1991

[30] Foreign Application Priority Data

Mar. 2, 1990 [DE] Fed. Rep. of Germany ....... 4006520

[51] Int. Cl.$^5$ .................. C07C 68/06; C07C 69/96
[52] U.S. Cl. ................................. 558/270; 558/265; 558/266; 558/267; 558/268; 558/269; 558/271; 558/272; 558/273; 558/274; 558/276
[58] Field of Search ............... 558/274, 270, 271, 272, 558/273, 276

[56] References Cited

U.S. PATENT DOCUMENTS 4,554,110 11/1985 Mark ...................................... 558/274
5,034,557 7/1991 Kiso et al. ............................ 558/274

FOREIGN PATENT DOCUMENTS 0338760 10/1989 European Pat. Off. .
2736062 2/1979 Fed. Rep. of Germany ...... 558/274
3445552 4/1985 Fed. Rep. of Germany .
3445555 4/1985 Fed. Rep. of Germany .

*Primary Examiner*—Vivian Garner
*Attorney, Agent, or Firm*—Sprung Horn Kramer & Woods

[57] ABSTRACT

Aromatic and aliphatic-aromatic carbonic acid diesters can be obtained by transesterification of carbonic acid diesters containing aliphatic ester groups if polymeric hydroxystannoxanes are employed as catalysts.

17 Claims, No Drawings

PROCESS FOR THE PREPARATION OF CARBONIC ACID DIESTERS CONTAINING AT LEAST ONE AROMATIC ESTER GROUP

BACKGROUND OF THE INVENTION

1. Field of the Invention

The invention relates to a process for the preparation of carbonic acid diesters containing at least one aromatic ester group from carbonic acid diesters containing at least one aliphatic ester group by catalysed transesterification, polymeric hydroxystannoxanes being employed as catalysts.

2. Description of the Related Art

The preparation of aromatic and aliphaticaromatic carbonic acid esters by transesterification starting from aliphatic carbonic acid esters and phenols is known in principle. This is an equilibrium reaction, the position of the equilibrium being shifted almost completely in the direction of the carbonic acid ester having aliphatic substituents. It is therefore relatively easy to prepare aliphatic carbonic acid esters from aromatic carbonic acid esters and alcohols, whereas the reaction in the reverse sense proceeds well only if very reactive and selective catalysts are available. There has therefore been no lack of attempts to develop suitable catalysts for the purpose mentioned. For example, strong bases, such as alkali metal hydroxide, have been proposed for transesterification of aliphatic carbonic acid esters with phenols. However, these catalysts have only a low reactivity and low selectivity, since carbon dioxide is split off to a considerable extent in a side reaction, ethers being simultaneously formed.

The Lewis acid catalysts from the group of metal halides or corresponding acyloxy, alkoxy and aryloxy compounds of Al, Ti, U, V, Zn, Fe and Sn recommended in DE-OS (German Published Specification) 2,528,412 and 2,552,907 for the preparation of aromatic carbonic acid esters are adequately active and selective only in the case of the titanium compounds. However, the titanium catalysts have the disadvantage that they colour the end products deep red to brown, which is an adverse characteristic above all in the case of products which are difficult to purify by distillation and recrystallization.

DE-OS (German Published Specification) 3,445,552 recommends polymeric tin compounds containing recurring structural units of the formula

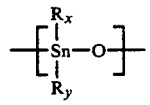

wherein
$R_x$ and $R_y$ each denote monovalent hydrocarbon radicals, for the transesterification mentioned.

SUMMARY OF THE INVENTION

It has now been found, surprisingly, that polymeric hydroxystannoxanes of the following formula (II) are considerably more effective as catalysts in the replacement of alkyl ester groups by aryl ester groups in carbonic acid diesters by transesterification than the polymeric tin catalysts of the above formula (I), a very high selectivity at the same time being achieved.

The invention accordingly relates to a process for the preparation of carbonic acid diesters containing at least one aromatic ester group from carbonic acid diesters containing at least one aliphatic ester group by catalysed reaction, which is characterized in that a polymeric hydroxystannoxane, or a mixture of several of these, containing monomeric units of the formula

in which
$R^1$ denotes straight-chain or branched $C_1$–$C_{18}$-alkyl, $C_3$–$C_8$-cycloalkyl, $C_6$–$C_{14}$-aryl, $C_7$–$C_{15}$-aralkyl or a $C_1$–$C_{18}$-alkylene radical or $C_6$–$C_{14}$-arylene radical bridging two polyhydroxystannoxane chains, is employed as the catalyst in an amount of 0.001–20% by weight, based on the carbonic acid diester employed which contains at least one aliphatic ester group.

DETAILED DESCRIPTION OF THE INVENTION

Straight-chain or branched $C_1$–$C_{18}$-alkyl is, for example, methyl, ethyl, propyl, isopropyl, butyl, isobutyl, t-butyl or the isomeric pentyls, hexyls, octyls (including 2-ethylhexyl), decyls, dodecyls, hexadecyls and octadecyls.

$C_3$–$C_8$-cycloalkyl is, for example, cyclopropyl, cyclopentyl, methyl-cyclopentyl, cyclohexyl, methylcyclohexyl, cycloheptyl or cyclooctyl.

$C_6$–$C_{14}$-aryl is, for example, phenyl, biphenylyl, naphthyl or anthryl.

$C_7$–$C_{15}$-aralkyl is, for example, benzyl, phenylethyl, phenylpropyl, phenylbutyl, naphthyl-methyl, naphthyl-ethyl or anthryl-methyl.

$C_1$–$C_{18}$-alkylene radicals which bridge two polyhydroxystannoxane chains can be straight-chain or branched and are, for example, linear or branched alkylene radicals, such as 1,2-ethylene, 1,2- or 1,3-propylene, 1,4-butylene, 1,6-hexylene and the like.

$C_6$–$C_{14}$-arylene radicals which bridge two polyhydroxystannoxane chains are, for example, 1,2-phenylene, 1,3-phenylene, 1,4-phenylene, 2,2'-biphenylene, 4,4'-biphenylene or other arylenes corresponding to the above aromatic radicals.

The radicals present in the substituents mentioned, in particular the aromatic radicals, can be mono-, di-, tri- or tetrasubstituted by $C_1$–$C_4$-alkyl, $C_1$–$C_4$-alkoxy, $C_1$–$C_4$-alkylthio, phenyl, phenoxy or phenylthio.

Polymeric hydroxystannoxanes of the formula

wherein
$R^2$ denotes straight-chain or branched $C_3$–$C_{12}$-alkyl, phenyl or benzyl
are preferably employed.

Mixtures of several hydroxystannoxanes can of course also be employed. Such a mixture can consist of hydroxystannoxanes which contain different substituents from the above scope of meaning. However, such a mixture can also consist of hydroxystannoxanes in which a different number of recurring monomer units of the above formula (II) or (III) is present. The number of recurring monomer units of the above formulae can be 3-30, preferably 3-20.

Particularly preferred polymeric hydroxystannoxanes are those containing monomer units of the formula

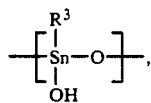  (IV)

in which

R$^3$ denotes straight-chain or branched C$_3$-C$_8$-alkyl.

Examples of polymeric hydroxystannoxanes which can be employed according to the invention are: poly(ethylhydroxystannoxane), poly(propylhydroxystannoxane), poly(butylhydroxystannoxane), poly(octylhydroxystannoxane), poly(methylhydroxystannoxane), poly(undecylhydroxystannoxane), poly(dodecylhydroxystannoxane), poly(phenylhydroxystannoxane), poly(4-methylphenylhydroxystannoxane) and poly(4-methoxyphenyl-hydroxystannoxane). Particularly important polymeric hydroxystannoxanes are, for example: (poly(propylhydroxystannoxane), poly(butylhydroxystannoxane) and poly(octylhydroxystannoxane).

The polymeric hydroxystannoxanes to be employed according to the invention are accessible, for example, in accordance with DE-AS (German Published Specification) 1,227,658 by alkaline hydrolysis of monoorganotintrihalides. When freshly prepared, they are preferentially in the trimeric cyclic form (six-membered ring), but are converted into species of higher molecular weight by storage, and more rapidly by heat treatment. During these processes, water is split off and in some cases crosslinking also occurs. The predominant cyclic oligomers contain no end groups; in the case of open-chain species, hydroxyl, alkoxy or halogen end groups or other end groups familiar to the expert are present.

The polymeric hydroxystannoxanes or a mixture of several of them are employed in a catalytic amount, for example in an amount of 0.001-20% by weight, preferably 0.005-5% by weight and particularly preferably 0.005-2% by weight, all amounts being based on the carbonic acid diester employed which contains at least one aliphatic ester group.

Catalysed transesterification according to the invention is to be understood as meaning the replacement of one or two aliphatic ester groups by one or two aromatic ester groups. This can be, for example, reaction of an aliphatic-aromatic carbonic acid diester with a phenol to give a purely aromatic carbonic acid diester, if appropriate containing two different aromatic ester groups. It can furthermore be the reaction of a purely aliphatic carbonic acid diester with a phenol to give an aliphatic-aromatic or a purely aromatic carbonic acid diester. In this case, one aliphatic ester group could first be replaced, for example by limiting the amount of phenol, and then the second aliphatic ester group could be replaced, if appropriate by a different phenol, so that carbonic acid esters containing two different aromatic ester groups are also obtainable here.

In the two cases mentioned, the more volatile aliphatic ester-alcohol is removed from the reaction mixture by distillation. Finally, the catalysed transesterification according to the invention can also be the disproportionation of a mixed aliphatic-aromatic carbonic acid diester to give a purely aromatic carbonic acid diester and a purely aliphatic carbonic acid diester, which can likewise be removed by distillation.

A bisphenol can also be employed as the phenol for the transesterification.

In the case of transesterification using a phenol, the weight ratio between the carbonic acid diester employed which contains at least one aliphatic ester group and such a phenol can vary within wide limits, for example from 1:99 to 99:1, preferably 1:9 to 9:1. Chiefly the diaryl-carbonic acid diester is formed in the case of a large excess of phenol, and in the case of a large excess of purely aliphatic carbonic acid diester, the mixed aliphatic-aromatic carbonic acid diester is preferentially formed. If bisphenols and at least 2 equivalents of carbonic acid diester are used, biscarbonates which still contain aliphatic or aromatic monoester groups on the molecule ends are formed. If approximately equivalent amounts of bisphenol and carbonic acid diester are employed, monocarbonates having a free phenolic hydroxyl group of the bisphenol are first obtained. Oligomeric or polymeric aromatic carbonates are formed from these under more severe reaction conditions. The variously substituted carbonic acid diesters can be separated from one another without problems, for example by distillation.

Carbonic acid diesters which contain at least one aliphatic ester group and are to be employed according to the invention are those of the formula

wherein

R$^4$ and R$^5$ independently of one another denote straight-chain or branched C$_1$-C$_{12}$-alkyl or C$_3$-C$_8$-cycloalkyl, and wherein R$^4$ can furthermore denote substituted or unsubstituted C$_6$-C$_{12}$-aryl.

In a preferred form, carbonic acid diesters of the formula

in which

R$^6$ and R$^7$ independently of one another denote straight-chain or branched C$_1$-C$_8$-alkyl, cyclopropyl, cyclopentyl or cyclohexyl, and wherein R$^6$ can furthermore denote substituted or unsubstituted phenyl, are employed.

Alkyl and cycloalkyl have the abovementioned scope of meaning. C$_6$-C$_{12}$-aryl is, for example, phenyl, biphenylyl or naphthyl, preferably phenyl. In the case of substitution of C$_6$-C$_{12}$-aryl, one or two substituents from the group comprising C$_1$-C$_4$-alkyl, C$_1$-C$_4$-alkoxy, cyano, fluorine, chlorine, bromine (chlorine is a preferred halogen) and nitro are possible.

Important carbonic acid diesters which are to be employed and contain two aliphatic ester groups are, for example: dimethyl carbonate, diethyl carbonate, dibutyl carbonate, diisopropyl carbonate, dicyclohexyl carbonate, dioctylcarbonate, and particularly preferably dimethyl and diethyl carbonate.

Important aliphatic-aromatic carbonic acid diesters which are to be employed are, for example: methyl phenyl carbonate, ethyl phenyl carbonate, butyl phenyl carbonate, methyl cresyl carbonate and their homologues.

In the case where the transesterification is carried out with the aid of a phenol, a phenol of the formula

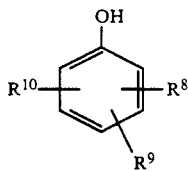  (VII)

in which
R$^8$ denotes hydrogen, C$_1$–C$_4$-alkyl, C$_2$–C$_4$-alkenyl, C$_1$–C$_4$-alkoxy, C$_5$–C$_6$-cycloalkyl, phenyl, fluorine, chlorine, bromine, cyano or nitro;
R$^9$ represents hydrogen, C$_1$–C$_4$-alkyl, C$_2$–C$_4$-alkenyl, C$_1$–C$_4$-alkoxy, fluorine, chlorine or bromine and
R$^{10}$ represents hydrogen, C$_1$–C$_4$-alkyl or the group

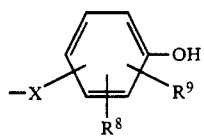

in which X denotes a single bond, —CH$_2$—, C$_2$–C$_5$-alkylene, C$_2$–C$_5$-alkylidene, C$_5$–C$_6$-cycloalkylene, C$_5$–C$_6$-cycloalkylidene, oxygen, sulphur, —CO—, —SO— or —SO$_2$—,
or wherein R$^9$ and R$^{10}$ together can also denote a fused-on benzene nucleus,
is employed.

Alkylene groups are bonded to the aromatic nuclei via two different C atoms, that is to say in 1,2-, 1,3-, 1,4-, 1,5-, 2,3- or 2,4-linkage; alkylidene groups are bonded to the aromatic nuclei via the same C atom, that is to say in 1,1-, 2,2- or 3,3-linkage. Cycloalkylene and cycloalkylidene can be substituted by 1 to 3 methyl or ethyl groups.

Monophenols which are preferably employed for the transesterification are those of the formula

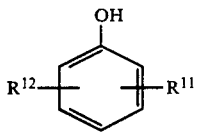  (VIII)

in which
R$^{11}$ and R$^{12}$ independently of one another denote hydrogen, C$_1$–C$_4$-alkyl, C$_5$–C$_6$-cycloalkyl or chlorine, and wherein R$^{11}$ can additionally denote nitro.

Examples of phenols which may be mentioned are: unsubstituted phenol, o-, m- or p-cresol, o-, m- or p-chlorophenol, o-, m- or p-ethylphenol, o-, m- or p-propylphenol, o-, m- or p-nitrophenol, 2,6-dimethylphenol, 2,4-dimethylphenol and 3,4-dimethylphenol.

Preferred bisphenols are those of the formula

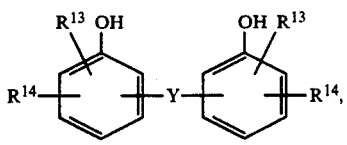  (IX)

in which

R$^{13}$ and R$^{14}$ independently of one another denote hydrogen, C$_1$–C$_4$-alkyl, C$_2$–C$_4$-alkenyl, C$_1$–C$_4$-alkoxy, C$_5$–C$_6$-cycloalkyl, fluorine, chlorine or bromine, and wherein R$^{13}$ can additionally denote nitro, and
Y represents a single bond, —CH$_2$—, C$_2$–C$_5$-alkylidene, C$_5$–C$_{10}$-cycloalkylidene, sulphur or —SO$_2$—.

Bisphenols which are particularly preferably employed for the transesterification are those in which X or y and the hydroxyl groups are in the o-, o'-, p-, p'- or o-,p'-position relative to one another.

Especially preferred bisphenols are those of the formulae

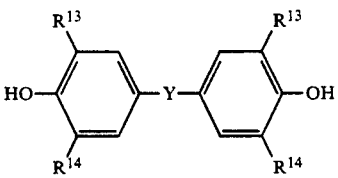  (X)

or

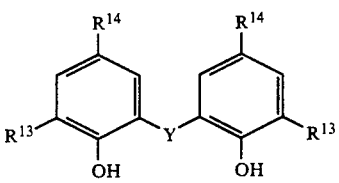  (XI)

or

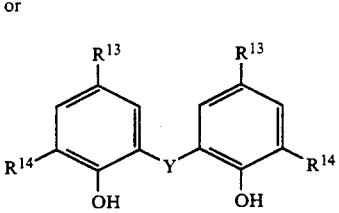  (XII)

in which R$^{13}$, R$^{14}$ and Y have the abovementioned meaning.

Examples of bisphenols which may be mentioned are: 2,2-bis-(4'-hydroxyphenyl)-propane (=bisphenol A), bis(4-hydroxyphenyl)-methane, 1,1-bis(4'-hydroxyphenyl)-cyclohexane, 2,2-bis(3'-5'-dimethyl-4'-hydroxyphenyl)-propane, 2,2'- and 4,4'-dihydroxy-biphenyl, bis(5-methyl-2-hydroxyphenyl)-methane, bis(3,5-dimethyl-2-hydroxyphenyl)-methane, bis(3-tert.-butyl-5-methyl-2-hydroxyphenyl)-methane, 1,1-bis-(4'-hydroxyphenyl-)3,5,5-trimethylcyclohexane. Amongst these, bisphenol A is particularly important.

Carbonic acid diesters which contain at least one aromatic ester group and are obtainable according to the invention are those of the formula

R$^{15}$O—CO—OR$^{16}$   (XIII), in which
R$^{15}$ and R$^{16}$ independently of one another can denote substituted or unsubstituted C$_6$–C$_{12}$-aryl, which can be substituted in the abovementioned manner, and wherein R$^{15}$ can furthermore denote straight-chain or branched C$_1$–C$_{12}$-alkyl or C$_3$–C$_8$-cycloalkyl.

The process according to the invention is carried out at a temperature of 50°–300° C., preferably 100°–250° C.

The pressure is in principle not critical and can be in a wide range of 0.5-50 bar, preferably 1-10 bar.

According to the invention, the reaction can be carried out without any solvent, that is to say in the melt of the substances to be reacted. However, it is likewise possible for the reaction to be carried out in a solvent which is inert in respect of the reaction. The procedure using such an inert solvent can be of importance, for example, if the aliphatic alcohol formed by the transesterification can be removed more easily from the reaction mixture with the aid of such a solvent. Solvents which are suitable according to the invention are, for example: aromatic (halogeno)hydrocarbons, such as toluene, xylenes, chlorobenzene, dichlorobenzenes, trimethylbenzenes and biphenyl, and (cyclo)aliphatic hydrocarbons, such as hexane, heptane, isooctane, cyclohexane, dekalin, ligroin and petroleum ether, and aliphatic and aromatic nitriles and ketones, such as acetone, acetonitrile, acetylbenzene, benzonitrile and others.

One possible procedure comprises bringing the transesterification mixture to the desired reaction temperature in an apparatus with an adequate column and distilling off, over the top, the aliphatic alcohol to be split off. In the case of disproportionation, in which the completely aromatic carbonic acid diester and the completely aliphatic carbonic acid diester are formed from an aliphatic-aromatic carbonic acid diester, the completely aliphatic carbonic acid diester, which is in general more volatile, can be distilled off over the top. The more volatile substance can be separated off in the manner described using an inert solvent or a stream of gas. It is furthermore possible for only some of one or both of the starting substances to be initially introduced into the reaction vessel and for the remainder to be metered into the melt or solution of the reaction mixture after the reaction has started up.

The examples which follow show the particularly increased catalytic reactivity of the polymeric hydroxystannoxanes according to the invention in comparison with the catalysts of the prior art mentioned in the introduction to the description.

EXAMPLES 1-5

General experimental instructions

A hot extraction apparatus consisting of a multi-necked sump flask, an extraction attachment (tube with inserted extraction casing) and reflux condenser was used to determine the catalytic activity of the particular catalyst under identical conditions. In each case a mixture of 29.5 g (0.25 mol) of diethyl carbonate and 47.1 g (0.50 mol) of phenol was brought to the boiling point in the sump flask so that the more volatile diethyl carbonate distilled into the extraction attachment and flowed uniformly through the extraction casing, in each case filled with 10 g of molecular sieve (Baylith TE 144 Bayer). The reaction was started by addition of the catalyst (1 m equivalent) to be investigated into the sump flask (time t=0), the ethanol formed being entrained out of the reaction mixture with the aid of diethyl carbonate and bonded selectively and permanently to the molecular sieve. The rates of reaction were determined by determination of the product formation (ethyl phenyl carbonate and diphenyl carbonate) as a function of the reaction time with the aid of gas chromatography (GC).

TABLE 1

(Examples 1 to 5)

| Example | Catalyst | t [h] | EPC[a] | DC[b] | EPC + DC | Discoloration of the reaction mixture |
|---|---|---|---|---|---|---|
| | | | all in % by area (GC) | | | |
| 1 (according to the invention) | [-Sn(Bu)(OH)-O-] | ¼ | 4.3 | 0.2 | 4.5 | very slight |
| | | ½ | 8.2 | 0.6 | 8.8 | |
| | | 1 | 13.9 | 1.9 | 15.8 | |
| | | 2 | 18.5 | 3.7 | 22.2 | |
| 2 (for comparison) | [-Sn(Bu)(Bu)-O-] | ¼ | 0.5 | — | 0.5 | slight |
| | | ½ | 0.9 | — | 0.9 | |
| | | 1 | 1.7 | 0.3 | 2.0 | |
| | | 2 | 3.5 | 0.6 | 4.1 | |
| 3 (for comparison) | Ti(OC$_2$H$_5$)$_4$ | ¼ | 1.7 | — | 1.7 | orange-red |
| | | ½ | 3.4 | 0.2 | 3.6 | |
| | | 1 | 6.5 | 0.7 | 7.2 | |
| | | 2 | 12.2 | 1.9 | 14.2 | |
| 4 (for comparison) | Sn(O-i-C$_8$H$_{17}$)$_4$ | ¼ | 0.3 | — | 0.3 | brown |
| | | ½ | 0.6 | — | 0.6 | |
| | | 1 | 1.2 | 0.1 | 1.3 | |
| | | 2 | 2.2 | 0.2 | 2.4 | |
| 5 (for comparison) | no catalyst | 2 | <0.1 | <0.1 | <0.1 | very slight |

[a]EPC = ethyl phenyl carbonate
[b]DC = diphenyl carbonate

The results of Examples 1-4 clearly show the considerably greater transesterification activity of the catalysts according to the invention in respect of the formation of both the aliphatic-aromatic ethyl phenyl carbonate and the diaromatic diphenyl carbonate in comparison with the polymeric tin catalysts from Example 2 (corresponding to DE-OS (German Published Specification) 3,445,552) or with the monomeric titanium alcoholates and tin alcoholates from Examples 3 and 4 (corresponding to DE-OS (German Published Specification) 2,528,412 and DE-OS (German Published Specification) 2,552,907). The only slight discoloration in comparison with the titanium esters according to Example 3 is also clearly to be seen.

EXAMPLES 6 TO 9

The transesterification of a mixture of 35.4 g (0.30 mol) of diethyl carbonate and 34.2 g (0.15 mol) of bisphenol A as a function of various catalysts (in each case 1 m equivalent) was investigated by the procedure described in Examples 1 to 5. The product formation (bisphenol A monoethyl carbonate and bisphenol A bisethyl carbonate) as a function of the reaction time was determined with the aid of gas chromatography (GC) as a measure of the rate of reaction.

TABLE 2

(Examples 6-9)

| Example | Catalyst | t [h] | BPA—MC$^{a)}$ | BPA—BC$^{b)}$ | BPA—MC + BPA—BC | Discoloration |
|---|---|---|---|---|---|---|
| 6 (according to the invention) | 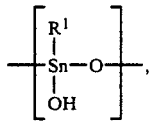 | ½ 1 2 | 0.5 3.9 13.6 | — 0.1 1.4 | 0.5 4.0 15.0 | very slight |
| 7 (for comparison) | Bu\|Sn—O\|Bu | ½ 1 2 | 0.9 2.6 4.5 | — — 0.2 | 0.9 2.6 4.7 | slight |
| 8 (for comparison) | $Sn(OiC_8H_{17})_4$ | ½ 1 2 | 0.1 0.2 0.5 | — — — | 0.1 0.2 0.5 | slight |
| 9 (for comparison) | $Ti(OC_{12}H_{25})_4$ | ½ 1 2 | only minimal reaction since precipitation of bisphenol A by the catalyst | | | orange precipitate |

$^{a)}$BPA—MC = bisphenol A monoethyl carbonate
$^{b)}$BPA—BC = bisphenol A bisethyl carbonate

What is claimed is:

1. A process for the preparation of carbonic acid diesters containing at least one aromatic ester group from the reaction of carbonic acid diesters containing at least one aliphatic ester group and phenols by catalysed transesterification, wherein one or more polymeric hydroxystannoxanes containing monomeric units of the formula

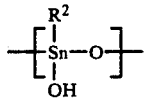

in which
  $R^1$ denotes straight-chain or branched $C_1$-$C_{18}$-alkyl, $C_3$-$C_8$-cycloalkyl, $C_6$-$C_{14}$-aryl, $C_7$-$C_{15}$-aralkyl or a $C_1$-$C_{18}$-alkylene radical or $C_6$-$C_{14}$-arylene radical bridging two polyhydroxystannoxane chains, are employed as the catalyst in an amount of 0.001-20% by weight, based on the carbonic acid diester employed which contains at least one aliphatic ester group.

2. The process of claim 1, wherein one or more polymeric hydroxystannoxanes containing monomer units of the formula $$\left[\begin{array}{c} R^2 \\ | \\ Sn-O \\ | \\ OH \end{array}\right]$$

in which
  $R^2$ denotes straight-chain or branched $C_3$-$C_{12}$-alkyl, phenyl or benzyl,
are employed.

3. The process of claim 2, wherein one or more polymeric hydroxystannoxanes, containing monomer units of the formula $$\left[\begin{array}{c} R^3 \\ | \\ Sn-O \\ | \\ OH \end{array}\right]$$

in which
  $R^3$ denotes straight-chain on branched $C_3$-$C_8$-alkyl are employed.

4. The process of claim 1, wherein the catalyst is employed in an amount of 0.005-5% by weight.

5. The process of claim 4, wherein the catalyst is employed in an amount of 0.005-2% by weight.

6. The process of claim 1, wherein a carbonic acid diester containing at least one aliphatic ester group, of the formula $$R^4O—CO—OR^5$$

in which
  $R^4$ and $R^5$ independently of one another denote straight-chain or branched $C_1$-$C_{12}$-alkyl or $C_3$-$C_8$-cycloalkyl, and wherein $R^4$ can furthermore denote substituted or unsubstituted $C_6$-$C_{12}$-aryl,
is employed.

7. The process of claim 6, wherein a carbonic acid diester containing at least one aliphatic ester group, of the formula $$R^6O—CO—OR^7$$

in which
  $R^6$ and $R^7$ independently of one another denote straight-chain or branched $C_1$-$C_8$-alkyl, cyclopropyl, cyclopentyl or cyclohexyl, and wherein $R^6$ can furthermore denote substituted or unsubstituted phenyl,
is employed.

8. The process of claim 1, wherein a phenol of the formula

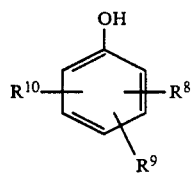

in which

R$^8$ denotes hydrogen, C$_1$-C$_4$-alkyl, C$_2$-C$_4$-alkenyl, C$_1$-C$_4$-alkoxy, C$_5$-C$_6$-cycloalkyl, phenyl, fluorine, chlorine, bromine, cyano or nitro;

R$^9$ represents hydrogen, C$_1$-C$_4$-alkyl, C$_2$-C$_4$-alkenyl, C$_1$-C$_4$-alkoxy, fluorine, chlorine or bromine and represents hydrogen, C$_1$-C$_4$-alkyl or the group

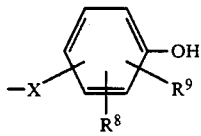

in which X denotes a single bond, —CH$_2$—, C$_2$-C$_5$-alkylene, C$_2$-C$_5$-alkylidene, C$_5$-C$_6$-cycloalkylene, C$_5$-C$_6$-cycloalkylidene, oxygen, sulphur, —CO—, —SO— or —SO$_2$—, or wherein R$^9$ and R$^{10}$ together can also denote a fused-on benzene nucleus, is employed for the transesterification.

9. The process of claim 8, wherein a phenol of the formula

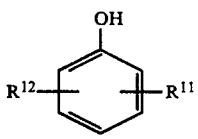

in which

R$^{11}$ and R$^{12}$ independently of one another denote hydrogen, C$_1$-C$_4$-alkyl, C$_5$-C$_6$-cycloalkyl or chlorine, and wherein R$^{11}$ can additionally denote nitro, is employed.

10. The process of claim 8, wherein a bisphenol of the formula

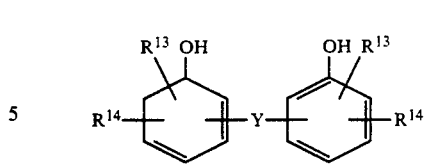

in which

R$^{13}$ and R$^{14}$ independently of one another denote hydrogen, C$_1$-C$_4$-alkyl, C$_2$-C$_4$-alkenyl, C$_1$-C$_4$-alkoxy, C$_5$-C$_6$-cycloalkyl, fluorine, chlorine or bromine, and wherein R$^{13}$ can additionally denote nitro, and Y represents a single bond, —CH$_2$—, C$_2$-C$_5$-alkylidene, C$_5$-C$_{10}$-cycloalkylidene, sulphur or —SO$_2$— is employed.

11. The process of claim 10, wherein a bisphenol of the formulae

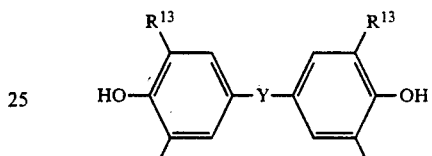

or

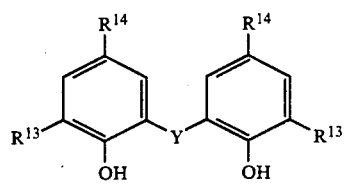

or

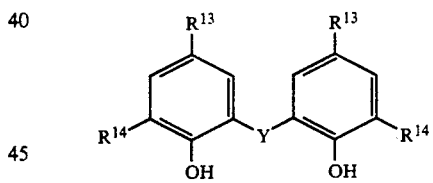

in which R$^{13}$, R$^{14}$ and Y have the meaning as indicated in claim 10, is employed.

12. The process of claim 1, which is carried out at a temperature of 50°-300° C.

13. The process of claim 12, which is carried out at a temperature of 100°-250° C.

14. The process of claim 1, wherein the polymeric hydroxystannoxane has 3-30 recurring polymeric units.

15. The process of claim 14, wherein the polymeric hydroxystannoxane has 3-20 recurring polymeric units.

16. The process of claim 1, which is carried out at a pressure of 0.5-50 bar.

17. The process of claim 16, which is carried out at a pressure of 1-10 bar.

* * * * *

UNITED STATES PATENT AND TRADEMARK OFFICE
CERTIFICATE OF CORRECTION

PATENT NO. : 5,149,856

DATED : September 22, 1992

INVENTOR(S) : Schon et al.

It is certified that error appears in the above-identified patent and that said Letters Patent is hereby corrected as shown below:

Col. 11, line 20   Before " represents " insert -- $R^{10}$ --

Col. 12, line 5    Delete " 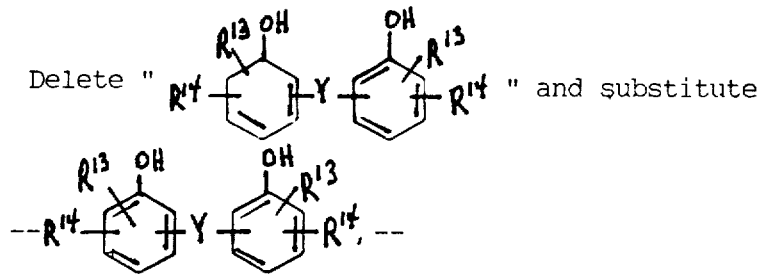 " and substitute

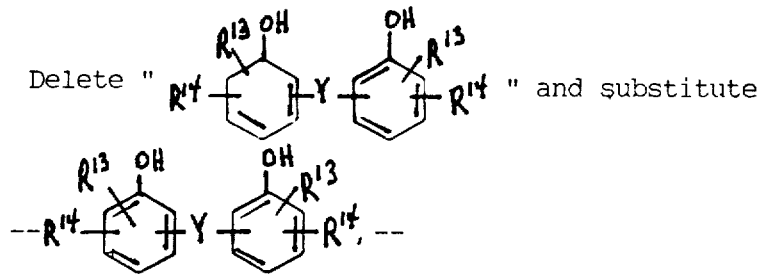

Signed and Sealed this

Twenty-sixth Day of April, 1994

*Attest:*

BRUCE LEHMAN

*Attesting Officer* — *Commissioner of Patents and Trademarks*